United States Patent [19]
Clawson

[11] Patent Number: 6,004,266
[45] Date of Patent: Dec. 21, 1999

[54] METHOD AND SYSTEM FOR THE HEART PROBLEM PROTOCOL OF AN EMERGENCY MEDICAL DISPATCH SYSTEM

[76] Inventor: Jeffrey J. Clawson, 4649 Farm Meadow La., Salt Lake City, Utah 84111

[21] Appl. No.: 08/825,611

[22] Filed: Mar. 28, 1997

Related U.S. Application Data

[60] Provisional application No. 60/014,741, Mar. 29, 1996.

[51] Int. Cl.[6] ................................................ G01F 15/42
[52] U.S. Cl. ............................................ 600/300; 128/903
[58] Field of Search .................................. 600/300, 301, 600/481, 483, 484, 485, 508, 509, 510, 513, 522; 364/413.02, 413.03

[56] References Cited

U.S. PATENT DOCUMENTS

| | | | |
|---|---|---|---|
| 3,799,147 | 3/1974 | Adolph et al. | 600/513 |
| 4,130,881 | 12/1978 | Haessler et al. | 364/900 |
| 4,237,344 | 12/1980 | Moore | 179/2 A |
| 4,489,387 | 12/1984 | Lamb et al. | 364/514 |
| 4,839,822 | 6/1989 | Dormond et al. | 364/513 |
| 4,858,121 | 8/1989 | Barber et al. | 364/406 |
| 4,945,476 | 7/1990 | Bodick et al. | 364/413.02 |
| 5,063,522 | 11/1991 | Winters | 395/51 |
| 5,065,315 | 11/1991 | Garcia | 364/413.01 |
| 5,072,383 | 12/1991 | Brimm et al. | 364/413.02 |
| 5,253,164 | 10/1993 | Holloway et al. | 364/406 |
| 5,255,187 | 10/1993 | Sorensen | 364/413.02 |
| 5,471,382 | 11/1995 | Tallman et al. | 364/406 |
| 5,544,649 | 8/1996 | David et al. | 600/511 |
| 5,596,994 | 1/1997 | Bro | 128/732 |
| 5,660,176 | 8/1997 | Iliff | 600/300 |
| 5,724,983 | 3/1998 | Selker et al. | 600/509 |

*Primary Examiner*—Robert L. Nasser
*Attorney, Agent, or Firm*—Lloyd W. Sadler

[57] ABSTRACT

A method and system for receiving, processing and responding to emergency medical calls for patients with heart problems is described. A consistent, standard and systematic process is provided which in combination with adequate training, supervision and quality assurance serves to provide a method for gathering emergency medical information regarding a patients heart problems, categorizing such information into various determinant levels for appropriate response, and for giving qualified emergency medical information to callers thereby permitting "zero time" response by those at the scene. By using this invention properly a dispatcher is guided through the interrogation of callers concerned with heart problems, gathering critical information and giving the appropriate guidance to the caller. This invention specifically guides the dispatcher through the steps of the heart problem protocol, thereby identifying the degree of urgency of heart problem complaints and appropriately dispatching emergency medical responders.

14 Claims, 5 Drawing Sheets

KEY QUESTIONS (701)

1. Does s/he have chest pain? — Y — 10
2. Is s/he breathing normally? — N — 6
3. Is s/he alert (able to talk)?
4. Has s/he had heart problems before?
   a. *(If yes)* Does s/he have a pacemaker or implanted defibrillator?
      i. *(If A.I.D.)* Did it fire (go off) in the last 30 minutes?
5. I want you to take her/his pulse (heart rate). *See Additional Information for instructions on taking a pulse.*
6. *(If suspected AND heart rate ≥ 100)* Did s/he take any drugs (medications) in the past 12 hours?
   a. Cocaine (or derivative)

POST-DISPATCH INSTRUCTIONS (704)

a. *Ensure ABCs.*
   1. *Assure airway.* — G1
   2. *Verify breathing.* — G4
   3. *Treat for shock.* — G8
b. Allow her/him to assume the most comfortable position for her/him.
c. If her/his condition worsens in any way, call me back immediately for further instructions.
d. If s/he is on any medications, please get them out for the paramedics. Write down the name and phone number of her/his doctor. Put any family dogs away. Can someone meet the paramedics please?

DETERMINANTS (703) / RESPONSES

A
   1    Heart rate < 130 (without priority symptoms)     1

B
   1    Unknown symptoms (3rd party situation)     1

C
   1    Not alert     1
   2    Cardiac history     2
   3    Heart rate ≥ 130 (without priority symptoms)     3
   4    Cocaine     4

D
   1    Firing of implanted defibrillator     1

*This section is for user-defined responses and modes only.*

DEFINITIONS – AXIOMS – RULES – LAWS

Instructions for Taking a Pulse (705)
1. "Find the Adam's apple on her/his neck.
2. Feel on either side of it for a pulse.
3. Be careful not to push too hard.
4. Count the pulses for 15 seconds (I'll time you).
5. How many did you count?" *(multiply x 4 = rate)*
   ≤ 25 x 4 = Rate < 100
   26-32 x 4 = Rate 100-129
   ≥ 33 x 4 = Rate > 130

Heart Attack, *Information Validation* (706)

*If there is a question of inaccurate information due to patient denial or caller confusion, the EMD may read the following to the person on the phone to help clarify the signs and symptoms of a possible heart attack:*

"Sometimes the symptoms of a heart attack are difficult to recognize. Many times it feels like severe indigestion. Other feelings may be tightness, heavy pressure, constricting band and crushing discomfort in the chest with the spread of these feelings to arms, jaw, neck or back. They may also be nauseated or sweating a lot. Are any of these feelings present?"

Rules (708)
1. The caller should be directed to take a pulse whenever it is physically possible (age, location, comprehension) using the appropriate "Instructions for Taking a Pulse" script.
2. If a patient has a very rapid heart rate (≥ 130) paramedics (ALS) should be sent.
3. Automatic Implanted (internal) Defibrillators (A.I.D.) are becoming more common. If reported as firing or causing problems, a maximum response is sent, as this may mean the patient is having significant arrhythmias or ventricular fibrillation (cardiac arrest will occur if unconverted by this device).

Axioms (707)
1. Heart Problems are considered a specific "diagnosis." Heart problem situations range from old rheumatic fever through benign forms of congestive heart failure to acute angina or serious heart attack (myocardial infarction). It is occasionally even reported as the chief complaint in cardiac arrest.
2. Obtain symptoms and medical history (through complete interrogation) which more accurately indicate the urgency of the problem and therefore can be prioritized.

METHOD AND SYSTEM FOR THE HEART PROBLEM PROTOCOL OF AN EMERGENCY MEDICAL DISPATCH SYSTEM

This application is based on Provisional Application Ser. No. 60/014,741, which was filed on Mar. 29, 1996, and priority is claimed thereto.

MICROFICHE APPENDIX

This specification includes a Microfiche Appendix which includes 1 page of microfiche with a total of 20 frames. The microfiche appendix includes computer source code and database structure of one preferred embodiment of the invention. In other embodiments of the invention, the inventive concept may be implemented in other computer code, in computer hardware, in other circuitry, in a combination of these, or otherwise. The Microfiche Appendix is hereby incorporated by reference in its entirety and is considered to be a part of the disclosure of this specification.

BACKGROUND OF THE INVENTION

1. Field of the Invention

This invention relates to methods and systems for processing and responding to emergency medical inquiries. Specifically, this invention relates to the process or method of managing the dispatch of emergency medical care to callers or patients with heart problem complaints. Providing adequate emergency medical care presents several critical challenges to medical care providers. These challenges include: the proximity to the care provider, the time required for help to arrive, the identification of the criticality of the emergency, the appropriate level of care provided, the variances in training of emergency medical dispatcher personnel, and limited nature of emergency care resources. This invention addresses these challenges by providing a consistent and proven system for: First, gathering necessary medical complaint information from emergency medical inquiry callers and providing emergency verbal instructions to individuals at the scene. Second, prioritizing the complaint to determine the criticality of the emergency. Third, assisting dispatched responders to be prepared for each emergency situation. Fourth, advising those on the way to provide care at the scene of specific problems or potential hazards. When used correctly this invention decreases the effective response time, while increasing the professionalism and control of emergency medical dispatchers, increases the accuracy and appropriateness of patient interrogation and well as the quality of gathered information, reduces the number of multiple unit responses thereby reducing the risk of emergency medical vehicular collisions, improves patient care, reduces burn-out and stress of dispatchers by improving their quality of training, decreases the risk of responder injury or mistake by providing responders with improved knowledge of the situation, and provides an means for continuously improving the quality of emergency patient care.

While being included within a greater invention that addresses all of the above issues, this invention specifically addresses the heart problem protocol or procedure. Heart problems constitute some of the most urgent and most dangerous of the emergency medical calls. Accurate, efficient and systematic responses to these calls can and does make the difference in the survival prospects of heart problem patients. This invention specifically addresses this problem.

2. Description of Related Art

It is desirable to provide a systematic and standardized method for responding to emergency medical requests. Although in the related art some attempt has been made to address the problem of medical care assessment, the related art does not address the specific problems of emergency dispatcher response to heart problem calls. Rather related art approaches describe the following. A process of helping patients assess their health, select appropriate health care, and guide such patients to an appropriate level and type of care. An automated medical history taking system and a technique wherein selected branch paths through a question repertory are provided. A method and apparatus for coordinating the actions of two or more medical teams, especially for instructional purposes. An expert system for providing suggested treatments for a patient with physical trauma. A medical payment system that incorporates computer technology in the storage, retrieval and processing of patient data and insurance claims. A knowledge base containing medical/pathological information on various diseases. A hospital computerized system for entering information pertinent to a patient's stay in the hospital. An expert computer system for processing medical claims. An interactive computerized apparatus and method for presenting medical information for diagnosis and study of disease. An automated and interactive positive motivation system to send a series of motivational messages and/or questions to a client to change or reinforce a specific behavioral problem. An artificial intelligent expert system. A rapid response health care communications system for providing rapid and reliable health services to patients located within or outside a health care facility.

For general background material, the reader is directed to U.S. Pat. Nos. 4,130,881, 4,237,344, 4,489,387, 4,839,822, 4,858,121, 4,945,476, 5,063,522, 5,065,315, 5,072,383, 5,253,164, 5,255,187, 5,471,382, and 5,596,994. Each of the above references is hereby incorporated by reference in its entirety for the material disclosed therein.

SUMMARY OF THE INVENTION

It is desirable to provide a system for emergency medical dispatch of health case services that provides the dispatcher a systematic method of interrogation of callers, where inquiries and instructions are pre-scripted, thus eliminating the variability due to different skills of the individual dispatchers and the need for the dispatcher to attempt to recall the appropriate inquiries and instructions each time a call is received. Furthermore, it is desirable to provide a system for emergency medical care dispatch that improves the accuracy and appropriateness of patient interrogation and resulting response generation. Such a system can formalize the roll of the emergency medical dispatcher as part of the professional chain of patient care. It is also desirable to have a method for communicating with medical response teams such that multiple unit and light-and-siren responses are reduced, thereby reducing the collision risks to emergency vehicles and preserving the limited emergency response resources. It is desirable to provide a medical dispatch system that improves patient care by improving the accuracy and usefulness of gathered information, thereby reserving paramedic teams for the most critical emergencies. It is desirable to have a medical dispatch system that reduces dispatcher burn-out and stress by improving information relayed to field responders while simultaneously providing such responders with increased safety awareness and knowledge of the field situation.

Accordingly, it is the primary object of this invention to provide a medical dispatch that is designed to guide the medical dispatcher through the interrogation, obtaining vital patient information regarding calls concerning patients with heart problems, including but not limited to rheumatic fever, cardiac arrest, congestive heart failure, acute angina, or serious heart attack (myocardial infarction).

Another object of this invention is to provide a cross-referenced scripted set of instructions to be given by the dispatcher to the caller in a medical emergency situation.

It is a further object of this invention to provide a method of determining the criticality of a medical emergency and communicating such level of criticality to the response personnel.

It is a still further object of this invention to provide a method for gathering and communicating information concerning the situation at the field location to the response personnel and the emergency medical callers.

A further object of this invention is to improve the quality, efficiency and usefulness of the information received to and communicated by emergency medical dispatchers thereby improving the quality of emergency medical services provided to patient before, during and after the arrival of emergency medical technicians.

These and other objects of this invention, which will be clear to those of ordinary skill in the art upon review of this patent specification and claims, are achieved by an invention which permits a systematic gathering of patient information, with a set of scripted instructions and with guidance for relaying information to the field emergency personnel. The method and system of this invention is currently envisioned in two equally preferred embodiments. First, a set of cross referenced cards with scripted questions, instructions and categorizations is provided. Second, a computerized process is provided with software controlling the access and reference points to a computerized database of emergency medical inquiries and instructions is provides. Each preferred embodiment incorporates the same essential method of this invention, though each has its own particular advantages.

BRIEF DESCRIPTION OF THE DRAWINGS

FIG. 7 depicts the preferred embodiment of the flip cards used as one embodiment of this invention, which shows the steps of the heart problem protocol of the flip card deck embodiment of the invention.

DETAILED DESCRIPTION OF THE INVENTION

This invention provides a method, system and an apparatus for receiving, processing and communicating emergency medical information, enabling an assessment of the critical or "key" information by trained emergency medical dispatch personnel. When the invention is properly employed the initial interrogation of the caller or patient will have previously provided the emergency medical dispatcher critical patient information which has indicated that the patient is most likely suffering from heart problems. This information is applied in this invention which leads the dispatcher through a scripted interrogation, gathering additional heart problem related information, categorizing the problem by assigning a determinant value establishing the criticality of the problem, and then providing appropriate scripted established emergency medical instruction to the individuals on the scene.

Figure 1:
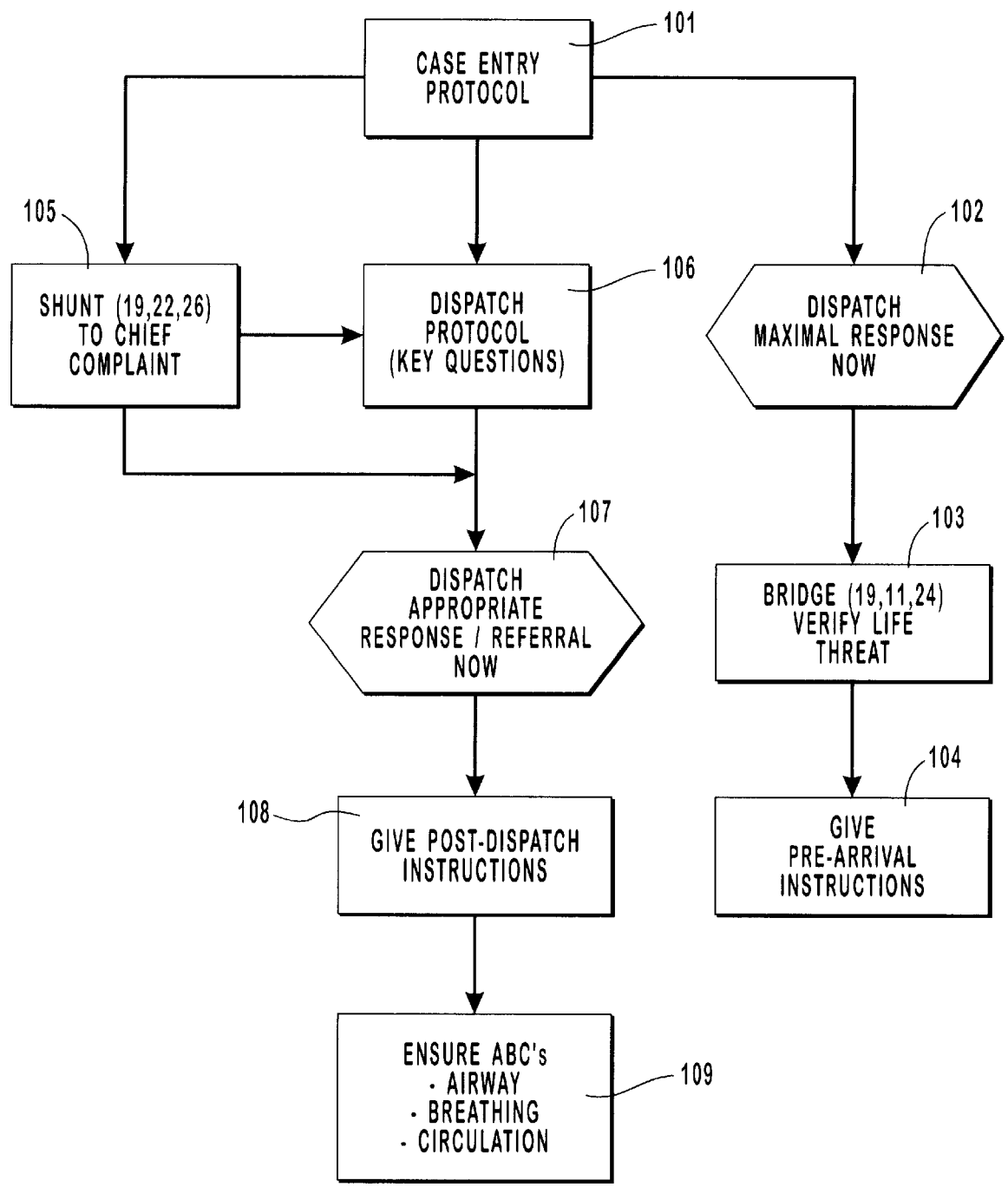
FIG. 1 depicts the principle elements of the complete system in which the preferred embodiment of the invention operates and the relationship of the elements of the system to each other and puts this invention into the context of the complete system.

FIG. 1 shows the complete system in which the invention operates in its best mode. The process of managing emergency medical dispatchers, the information they require and the information they give is detailed in FIG. 1. The case entry protocol 101 provides the initial steps through which the all emergency callers or patients are taken to provide symptom information and to access medical information. The purpose of the case entry protocol 101 is to receive sufficient information to permit the dispatcher to identify the caller's chief complaint This critical information received during the primary interrogation 101 includes a description of the problem (or the patient's complaint), the patient's age and the status of consciousness and breathing. This information is also referred to as "the four commandments of emergency medical dispatching." If the dispatcher receives information that the patient is unconscious and not breathing (or unconscious and breathing is uncertain or conscious but not breathing where the failure to breath has been verified), for whatever reason, a maximal response 102 is sent immediately, before continuing with any further interrogation or instructions, and the caller is told to stay on the line for further instructions. A maximum response dispatch 102 may include such resources as emergency medical technicians, ambulances, paramedics, and other appropriate medical care givers. The life threat is then verified 103 and pre-arrival instructions are given 104. These pre-arrival instructions 104 include six treatment sequence scripts covering Arrest, Choking, and Childbirth. Instructions 104 are given to guide the caller through CPR, the Heimlich Maneuver, or emergency childbirth procedures. In many cases, the result of properly conveyed instructions is a more viable patient by the time field personnel arrive. Should the dispatcher learn that the patient is breathing, but the dispatcher lacks sufficient information to directly go to the Key Questions of the Dispatch Protocol 106, the dispatcher is shunted 105 to additional interrogations whose purpose is to give the dispatcher the necessary information to ascertain the caller's chief complaint while focusing on heart problems, industrial/machinery accidents and/or general sick person issues. The process and procedure for the heart problems shunt is the heart of this invention. Once the dispatcher has enough information to have identified the caller's chief complaint, the dispatcher is taken to the Dispatch Protocol 106 where additional interrogations are performed to complete "key questions." This secondary interrogation 106 typically takes approximately 30 seconds and tends to focus on the specific or chief complaint of the caller. This secondary interrogation, or Dispatch Protocol 106, provides a more orderly and closer view of the patient so that the pre-hospital care provided is appropriate and in keeping with the severity of the injury or illness. During this step 106 the dispatcher will match the symptoms, or combination of symptoms, discovered through interrogation and send the appropriate response 107. The appropriate response 107 is determined through a system of assigning determinant levels and numbers, from A2 generally less serious to D1 generally very serious. When the dispatcher identifies a determinant in one of the four levels (Alpha—A, Bravo—B, Charlie—C, and Delta—D) the response configuration (emergency vehicles and the mode of response) is dispatched as indicated by the response protocol. After the responders (field emergency medical care-givers) has been sent, the dispatcher remains on the telephone with the caller to give instructions 108 regarding what to do, and what not to do, prior to the arrival of the responders. This information is taken from the "Post-Dispatch Instructions" section of the protocols and provided whenever possible and appropriate. A main purpose of these "Post-Dispatch Instructions" 108 is to prepare the patient for and to expedite the field personnel's work at the scene. "Post-Dispatch Instructions" include such instructions as to collect the patient's medications, write down the name of the family doctor and put away pets. Each caller is also instructed to ensure 109 that the patient has an open airway, is breathing, is given nothing to eat or drink before responders arrive and, if necessary, how to treat for shock using the procedure given in the reference script for Airway, Breathing, and Circulation. Callers are routinely advised to "call back if the patient's condition worsens for further instructions."

Figure 2:
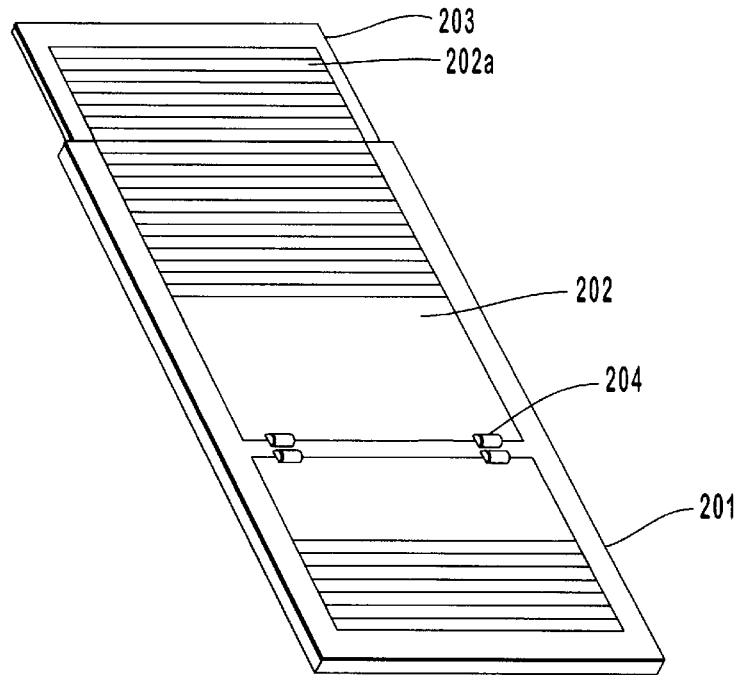
FIG. 2 depicts the flip card apparatus showing a preferred embodiment of the invention.

FIG. 2 depicts an embodiment of the flip card apparatus showing a preferred system for the use of the invention. One preferred embodiment of the invention involves the use of a flip card apparatus 201. The flip card apparatus 201 has the advantage of organizing the cards 202 so that the top or bottom, label edge of each card can be seen by the user. Each card 202 is separately fastened into the apparatus with one or more fasteners 204. The steps embodying the elements of this invention, the entry protocol, are displayed on a top flap 203 and the first card 202a. Alternative embodiments of the card apparatus can be a deck of cards bound in a manner well known to those skilled in the art. In the current embodiment of the flip card apparatus there are sixty-four chief complaint cards, twelve pre-arrival instruction cards, two post-dispatch cards, one determinant classification card and two entry protocol cards. The cards are generally organized in pairs, with the top card providing the protocol questions, instructions, jump directions and determinant assignments. The bottom card provides information the dispatcher uses to improve the dispatcher's decision making process.

Figure 3:
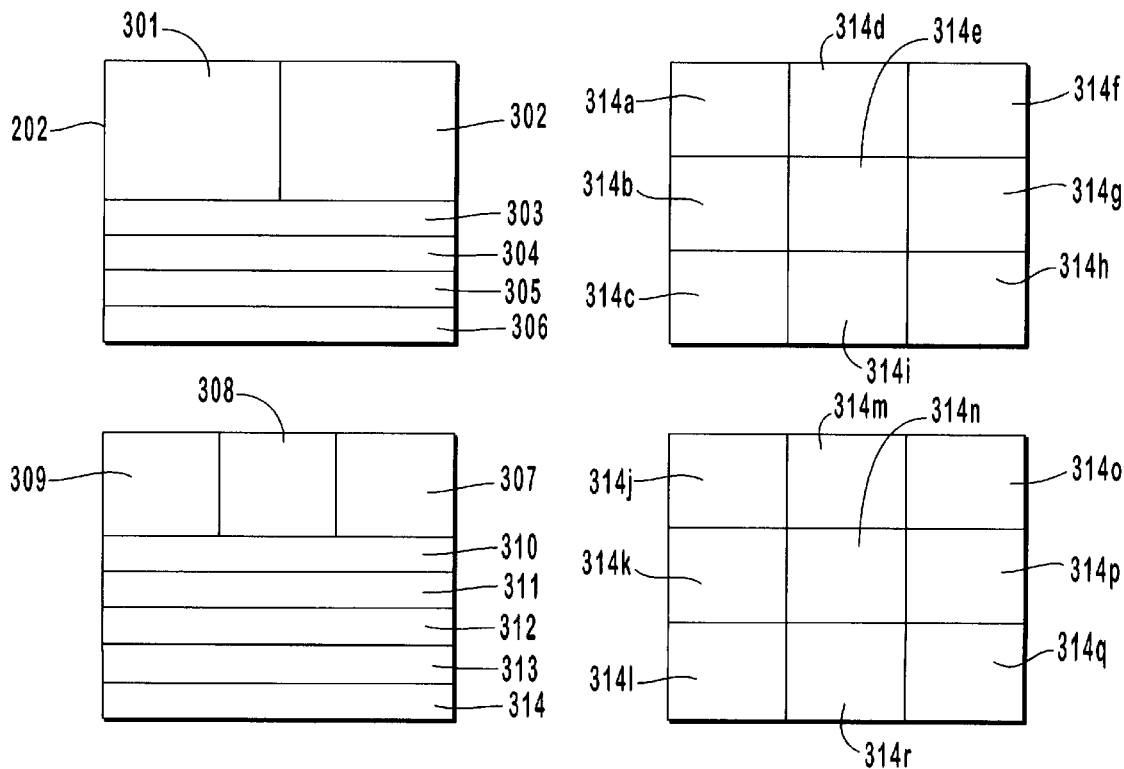
FIG. 3 shows a view of the sections of a typical flip card as used in the flip card apparatus embodiment of the invention.

FIG. 3 shows a view of the sections of a typical flip card, as used in the flip card apparatus embodiment of the invention. The typical flip card 202 is divided into logical sections for ease of use and consistency. A key question section 301 is provided as a script to the dispatchers to ensure that all key questions are asked in a calm, consistent, systematic manner. After all key questions are asked from the key question section 301, typically the dispatcher determines the appropriate determinant level. Sections A-Alpha 303, B-Bravo 304, C-Charlie 305 and D-Delta 306 are provided to aid the dispatcher in making the determinant designation. Each determinant level may have one or more sublevels. Generally, the most critical call is given a determinant level of D-Delta and the least critical call is given a determinant level of A-Alpha The more critical the determinant level assigned to a call, the more medical resources and urgency may be applied to provide help. For example, an A-Alpha call will typically be responded to by emergency medical technicians and an ambulance proceeding to the patient under the safest method reasonably possible, while a D-Delta call will typically be responded to by the closest emergency medical technicians, an ambulance, paramedics, all who will proceed under the most urgent method possible. Sublevels may not indicate the criticality of the call, rather sublevel designations indicate the type of call, information often especially important to the dispatched medical team. After the determinant code is determined 303–306 the dispatcher is referred to the post-dispatch instructions section 302. The purpose of the post-dispatch instructions is to systematically prepare for and expedite the field personnel's job at the scene and prevent further harm to the patient or others at the scene. The post-dispatch instruction section 302 includes such instructions as collecting the patient's medications, writing down the name of the family doctor and securing animals in the area. Each caller is also instructed, from the post-dispatch instruction section 302, to ensure that the patient has an open airway, is breathing, is given nothing to eat or drink before responders arrive, and, if needed, how to treat for shock using a reference script. Callers are also routinely advised to "call back if the patient's condition worsens for further instructions." Pre-arrival instructions 106 are provided on alternative sections 314, subsectioned as shown in FIG. 3 as 314 a–r. These pre-arrival instruction sections 314 provide scripted treatment sequences for arrest, choking and childbirth. These procedures, provided through sections 314, guide the caller through CPR, the Heimlich Maneuver or emergency childbirth procedures. Sections 307 to 314 provide important information to the dispatcher for the dispatcher's use in providing more educated responses. This information includes such information as categorizations of dangerous areas or injuries; types of injuries; symptoms; rules and axioms. Such information as is systematically provided to place the key questions of section 301, the determinant classifications of sections 303–306, and the post-dispatch instructions of section 302 into context for the dispatcher.

Figure 4:
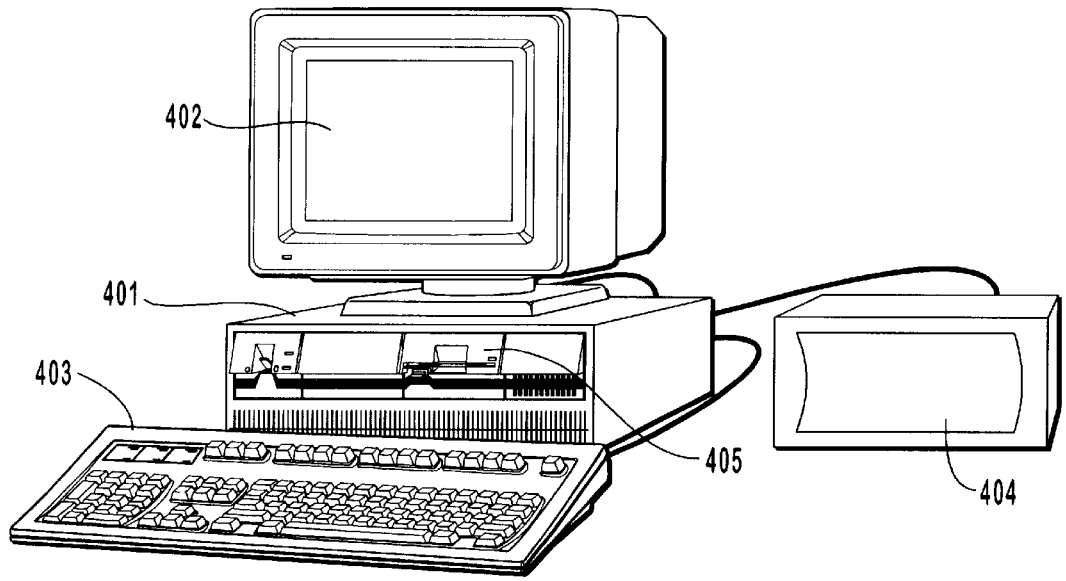
FIG. 4 shows a system diagram showing the components of a typical computer system used in the computerized embodiment of the invention.

FIG. 4 shows a system diagram of the components of a typical computer system used in the computerized embodiment of the invention. A second preferred embodiment of the invention is designed to operate in combination with a computer system using specially designed computer software incorporating the procedure of the invention. A typical computer system used in combination with software incorporating the invention includes a processing unit 401 to execute the instructions of the software; a display unit 402 to provide the means for providing the dispatcher with the prompts and information necessary to practice the invention; an input device 403 to provide the means for the dispatcher to interact with the software version of the invention; a storage device 405 for storage of the software and the files associated with the invention; and an output device 404 for printing reports and other information.

Figure 5:
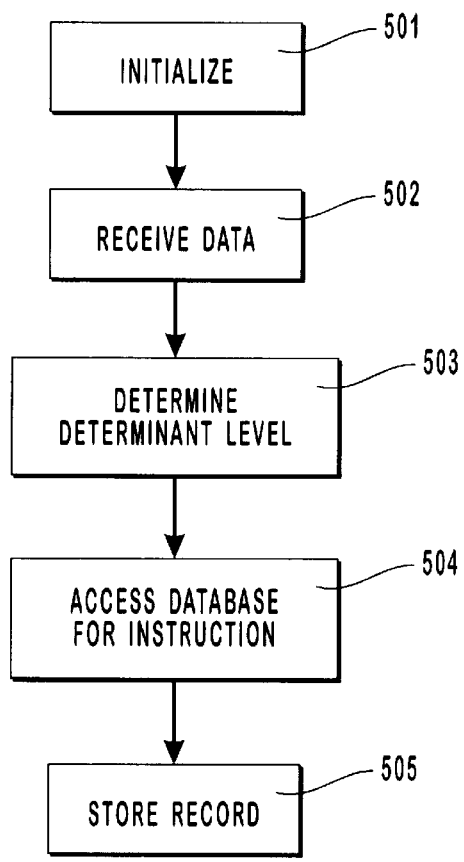
FIG. 5 shows a flow chart representation of the preferred top level steps of the invention.

FIG. 5 shows a process flow chart representation of the preferred top level steps of the invention. The software embodiment of the procedure of the invention is accomplished by performance of a number of procedural steps. First, the software is initialized 501. Data is received 502 following the request for information from the caller. As data is received 502, the determinant level is determined 503. Intermediate determinant levels are produced as information is received and processed, the final determinant level is only achieved after all necessary information is received and processed. A data base is accessed 504 to produce the appropriate instructions for communication with the caller. Records of the calls and queries are stored 505, for historical reports, for review of the dispatchers and for continued quality assurance control.

Figure 6:
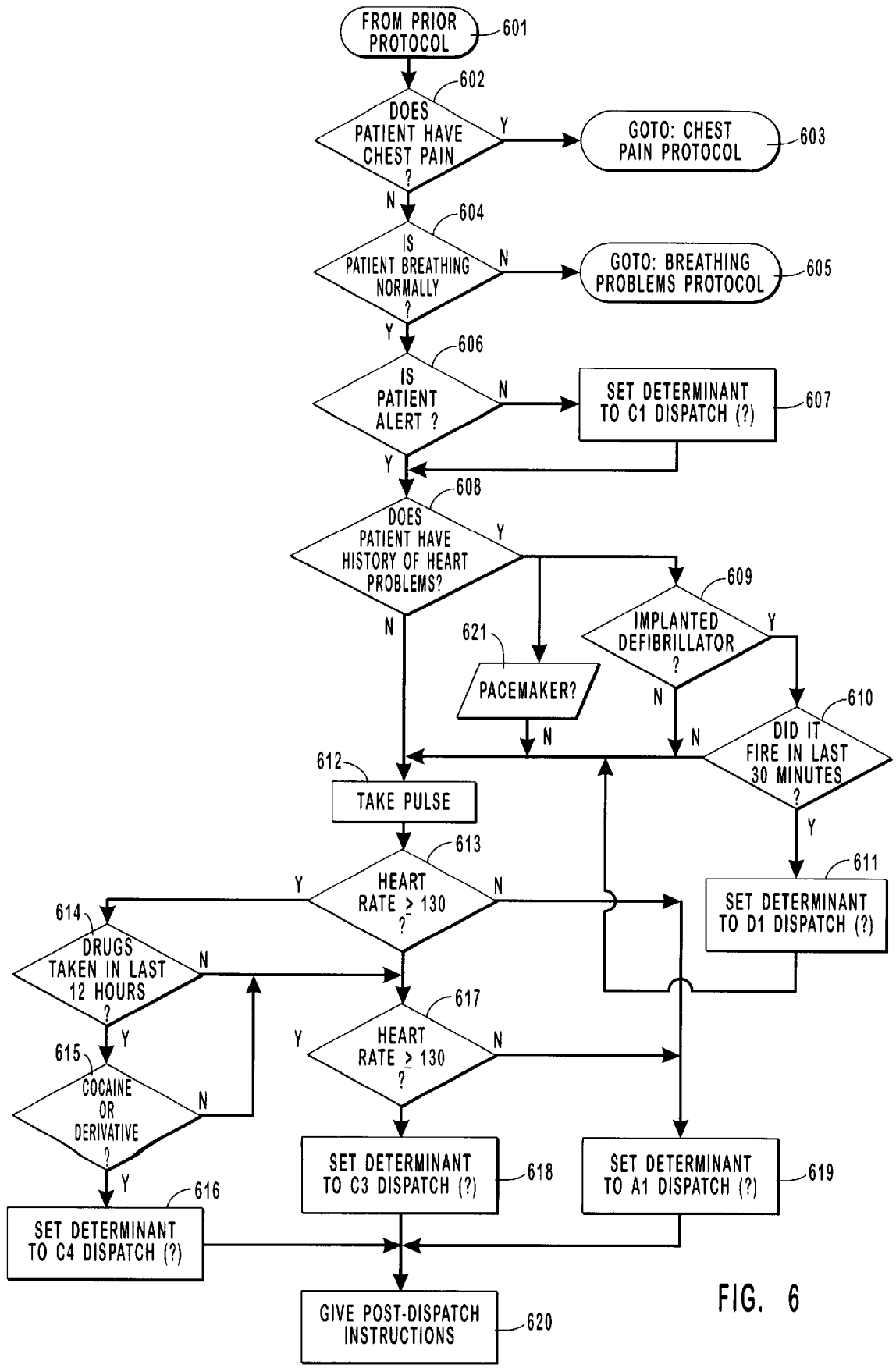
FIG. 6 depicts the detailed steps of the heart problems protocol process of the preferred embodiment of the invention.

FIG. 6 depicts the detailed steps of the heart problem protocol process of the preferred embodiment of the invention. Although the following steps of the process of the invention need not be accomplished in this specific order, alternative ordering of the steps of the invention are possible, this order of the steps of the process has been determined by the inventor to be the best mode of the invention. First, this protocol is reached by dispatchers after a prior protocol has been used to learn preliminary information 601. This prior protocol will provide, at a minimum, the following information: a description of the medical problem; the age of the patient; whether the patient is conscious; and whether the patient is breathing. This information, along with other information acquired during the process of this invention is used to assign determinants of criticality to the emergency as well to make important decisions as to the appropriate response and instructions which should be provided to the individuals at the scene. Next, it is determined whether the patient has chest pain 602. If chest pain is reported, then a branch is made to the specific complaint protocol for chest pain 603. If no chest pain is reported, then it is determined whether the patient is breathing normally 604. If the patient is not breathing normally, then a branch is made to the protocol for the specific complaint for breathing problems 605. The question is then asked, whether the patient is alert 606. Alert is defined as being able to talk. If the patient is described as not alert the determinant value is set to C1 and the dispatcher has the option of dispatching a medical response team to the patient 607. Next, the inquiry is made as to whether the patient has had heart problems before 608. If the patient has a history of heart problems then the procedure inquires as to whether the patient has a pacemaker 621 or an implanted defibrillator 609. If the patient has an implanted defibrillator, an inquiry is made as to whether it "fired off" during the previous thirty minutes 610. If it has "fired off" during the previous thirty minutes, this may mean that the patient is having significant arrhythmias or ventricular fibrillation, that is cardiac arrest may occur, therefore the determinant value is set to D1 and a maximum response is dispatched 611. Next, the caller is instructed to take the patient's pulse 612. The following instructions are typically provided for taking a pulse: (1) find the patient's Adam's apple on his or her neck; (2) feel on either side of it for a pulse; (3) be careful not to push too hard; and (4) count the pulses for 15 seconds. Multiply the count by 4 to get the patient's heart rate. If the patient's heart rate 613 is greater than 100 then the inquiry is made as to whether the patient has taken any drugs during the last twelve hours 614. If the patient has taken drugs within the past twelve hours then a determination if the drug was cocaine or any of its derivatives is made 615. If the determination is made that the patient has used cocaine or any of its derivatives then the determinant is set to C4 and the dispatcher has the option of dispatching an emergency medical response team to the patient 616. If, however, the determination is made that either no drugs were take in the last twelve hours or the drug taken was not cocaine or any of its derivatives, then if the patient's heart rate 617 is greater than 130, the determinant is set to C3 and the dispatcher has the option of dispatching an emergency medical response team to the patient 618, typically, where a heart rate greater than 130 is detected, paramedics should be sent. If the heart rate is less than 130 and no drugs or no cocaine was taken by the patient, or if the patient's heart rate is less than 100 then the determinant is set to A1 and the dispatcher is given the option of dispatching an emergency medical response team to the patient 619. Next, the dispatcher gives the "Post-Dispatch" instructions 620. Such instructions will typically include instructing the caller to assure that the patient has a clear airway, is breathing, and is treated for shock. The patient should assume the most comfortable physical position. If the patient's condition worsens in any way, the caller is instructed to call back the dispatcher immediately for further instructions. If there is a question of inaccurate information due to patient denial or caller confusion, the dispatcher may instruct the caller that: "Sometimes the symptoms of a heart attack are difficult to recognize. Many times it feels like severe indigestion. Other feelings may be tightness, heavy pressure, constricting band and crushing discomfort in the chest with the spread of these feelings to the arms, jaw, neck or back. A heart attack patient may also be nauseated or sweating a lot. Are any of these feelings present?"

FIG. 7 depicts the preferred embodiment of the flip cards showing the steps of the heart problems protocol invention. Six key questions are shown in the "Key Questions" section 701. A "GO TO" column 702 is provided to prompt emergency medical dispatchers to other relevant protocols. The "Determinants" section 703 is given to guide the dispatcher to the appropriate determinant level based on the responses given to the "Key Questions" 701. Post-Dispatch instructions 704 are provided, guiding the dispatcher through emergency medical advice. Instructions for taking a pulse are provided 705, as is general information and script specific to heart attacks 706. Axioms 707 and rules 708 are provided to put the questions into context for the dispatchers.

It is to be understood that the above-described embodiments are merely illustrative of numerous and varied other embodiments which may constitute applications of the principles of the invention. Such other embodiments may be readily devised by those skilled in the art without departing from the spirit or scope of this invention and it is our intent that they be deemed within the scope of our invention.

I claim:

1. A method for managing the process of responding to calls concerning a patient's heart problems and for dispatching medical assistance to said patient, comprising the steps of:

(A) providing instructions to an emergency medical dispatcher, including instructions to inquire for specific information, receive complaint information, and to use such specific information in said method to determine a degree of criticality;

(B) inquiring for specific medical information;

(C) instructing a caller in determining whether the patient has chest pain, and receiving information regarding whether the patient has chest pain;

(D) instructing said caller in determining whether the patient is breathing normally, and receiving information regarding whether the patient is breathing normally;

(E) instructing said caller in determining whether the patient has had heart problems before, wherein if the patient has had heart problems before instructing said caller in determining whether the patient has an artificial device for managing the heart and where if the patient has said artificial device, it is determined whether said artificial device has fired off, and receiving information regarding whether the patient has had heart problems before, whether the patient has an artificial device, and whether said artificial device has fired off;

(F) instructing said caller in taking the patient's pulse, and receiving information regarding the patient's pulse;

(G) setting a determinant value based on said received information, including whether the patient is alert, whether the patient has said artificial device fire off, and based on the patient's heart rate; and (H) directing a dispatch of emergency medical service wherein said dispatch urgency and type is determined by said determinant value.

2. A method as recited in claim 1 further comprising the step of:

(g) giving medical instructions.

3. A method as recited in claim 1 wherein said setting appropriate determinant value step further comprises the steps of:

(i) asking whether the patient's heart rate is greater than 100;

(ii) if the patient's heart rate is greater than 100, asking whether the patient has taken drugs;

(iii) checking whether the patient's heart rate is greater than 130; and (iv) setting a determinant value based on the patient's heart rate and whether the patient has used drugs.

4. A method as recited in claim 1 wherein said step of determining whether the patient has chest pain further comprises asking specific chest pain questions if the patient does have chest pain.

5. A method as recited in claim 1 wherein said step of determining whether the patient is breathing normally further comprises asking specific chest pain questions if the patient is not breathing normally.

6. A method for managing a medical inquiry process of an emergency medical dispatch system concerning calls regarding a patient's heart problems and for dispatching medical assistance to said patients needing medical assistance, the method comprising:

(A) making a first inquiry as to whether a patient, having a complaint concerning a patient's heart, has had prior heart problems;

(B) making a second inquiry, if the patient has had prior heart problems, as to whether the patient has an artificial device for managing the patient's heart;

(C) making a third inquiry, if the patient has an artificial device for managing the patient's heart, as to whether the artificial device has fired off;

(D) setting a determinant value to a high level of criticality if the artificial device has fired off; and (E) a dispatch of emergency medical assistance to said patient, wherein said dispatch is based on said determinant value.

7. A method as recited in claim 6, further comprising:

(e) instructing the patient's pulse and setting the determinant value inquiry based on said patient's pulse.

8. A method as recited in claim 6 further comprising:

(f) testing for whether the patient has chest pain.

9. A method as recited in claim 6 further comprising:

(g) testing for whether the patient is breathing normally.

10. A method as recited in claim 6 further comprising:

(h) testing for whether the patient is alert.

11. A method as recited in claim 6 wherein said artificial device is a pacemaker.

12. A method as recited in claim 6 wherein said artificial device is a implanted defibrillator.

13. A method for managing the process for responding to an emergency medical call relating to a patient's heart problems in a general purpose computer system comprising:

a central processing unit;

dynamic memory;

static memory;

a display device;

an input device;

an output device;

a mass storage device which contains
 a number of emergency medical instruction records,
 a number of medical information records,
 a grouping of determinant codes,
 a number of emergency medical inquiry reports, the method comprising the steps of:

(A) testing whether the patient has had prior heart problems, and receiving and storing in dynamic memory a result of said test;

(B) testing whether the patient has an artificial device for managing the patient's heart, and receiving and storing in dynamic memory a result of said test;

(C) testing whether the patient's artificial device for managing the patient's heart has fired off, and receiving and storing in dynamic memory a result of said test;

(D) setting a dispatch code, by said central processing unit, for the dispatch of emergency medical care to the patient based on the result of the test as to whether the patient's artificial device has fired off; and (E) dispatching emergency medical care to the patient based on said dispatch code.

14. In a general purpose computer system, a method as recited in claim 13 further comprising the steps of:

(e) testing whether the patient has chest pain;

(f) testing whether the patient is breathing normally; and (g) testing whether the patient is alert.

* * * * *